United States Patent
Uji et al.

(10) Patent No.: US 9,351,650 B2
(45) Date of Patent: May 31, 2016

(54) IMAGE PROCESSING APPARATUS AND IMAGE PROCESSING METHOD

(71) Applicant: CANON KABUSHIKI KAISHA, Tokyo (JP)

(72) Inventors: Akihito Uji, Kyoto (JP); Hiroshi Imamura, Kyoto (JP)

(73) Assignee: Canon Kabushiki Kaisha, Tokyo (JP)

( * ) Notice: Subject to any disclaimer, the term of this patent is extended or adjusted under 35 U.S.C. 154(b) by 116 days.

(21) Appl. No.: 14/182,677

(22) Filed: Feb. 18, 2014

(65) Prior Publication Data

US 2014/0240668 A1 Aug. 28, 2014

(30) Foreign Application Priority Data

Feb. 28, 2013 (JP) ................................. 2013-040039

(51) Int. Cl.
| | |
|---|---|
| *A61B 3/14* | (2006.01) |
| *A61B 3/00* | (2006.01) |
| *A61B 5/026* | (2006.01) |
| *G06K 9/00* | (2006.01) |
| *A61B 3/10* | (2006.01) |
| *A61B 3/12* | (2006.01) |

(52) U.S. Cl.
CPC ............. *A61B 5/0261* (2013.01); *A61B 3/1025* (2013.01); *A61B 3/1241* (2013.01); *A61B 3/14* (2013.01); *G06K 9/00127* (2013.01)

(58) Field of Classification Search
USPC .................................................. 351/206, 246
See application file for complete search history.

(56) References Cited

U.S. PATENT DOCUMENTS

| 4,425,924 A | 1/1984 | Riva et al. |
|---|---|---|
| 6,588,901 B1 | 7/2003 | Grinvald et al. |
| 2006/0147897 A1 | 7/2006 | Grinvald et al. |
| 2008/0247622 A1 | 10/2008 | Aylward et al. |
| 2008/0312533 A1 | 12/2008 | Balberg et al. |
| 2011/0137157 A1 | 6/2011 | Imamura et al. |
| 2012/0063660 A1 | 3/2012 | Imamura et al. |

(Continued)

FOREIGN PATENT DOCUMENTS

| EP | 2455912 A1 | 5/2012 |
|---|---|---|
| JP | 2008-104628 A | 5/2008 |

OTHER PUBLICATIONS

Akihito Uji, "Observation of dark tail in diabetic retinopathy uising adaptive optics scanning laser ophthalmoscope", Proceedings of the 66th Annual Congress of Japan Clinical Ophthalmology, 2012, p. 27.

(Continued)

*Primary Examiner* — Jack Dinh
(74) *Attorney, Agent, or Firm* — Fitzpatrick, Cella, Harper & Scinto

(57) ABSTRACT

An image processing apparatus obtains an image of an eye area, determines a measurement target among multiple vascular branches based on information regarding multiple vascular branches that include multiple vascular bifurcations in the obtained image, and measures the size of a blood cell aggregate in the determined measurement target.

17 Claims, 9 Drawing Sheets

(56) References Cited

U.S. PATENT DOCUMENTS

| | | |
|---|---|---|
| 2012/0063663 A1 | 3/2012 | Kawasaki |
| 2012/0130270 A1 | 5/2012 | Imamura et al. |
| 2012/0194782 A1 | 8/2012 | Imamura |
| 2012/0218517 A1 | 8/2012 | Imamura |
| 2013/0058553 A1 | 3/2013 | Yonezawa et al. |
| 2013/0265543 A1 | 10/2013 | Iwase et al. |
| 2014/0085606 A1 | 3/2014 | Miyasa et al. |
| 2014/0240669 A1 | 8/2014 | Imamura |

OTHER PUBLICATIONS

May 27, 2014 European Search Report in European Patent Appln. No. 14156225.6.

May 26, 2014 European Search Report in European Patent Appln. No. 14156223.1.

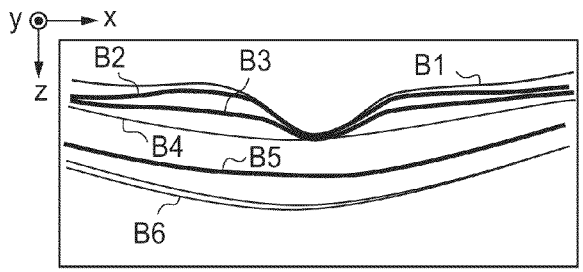
F I G. 6A
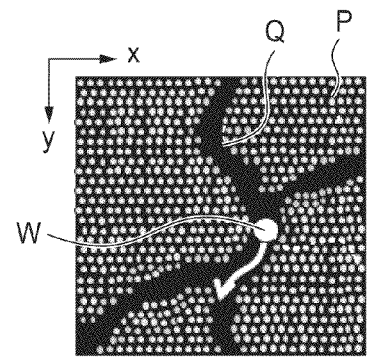
F I G. 6B
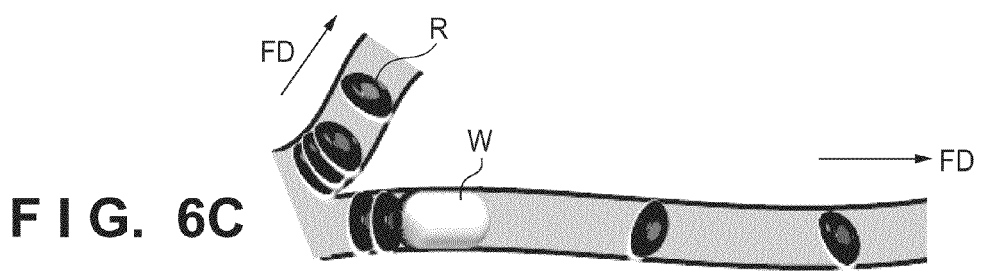
F I G. 6C
F I G. 6D
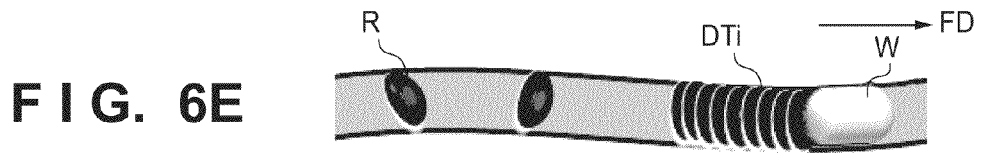
F I G. 6E
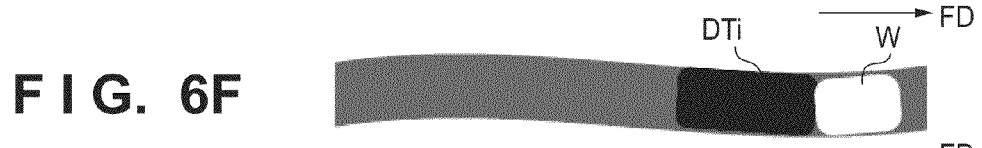
F I G. 6F
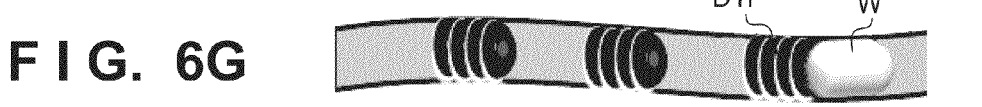
F I G. 6G

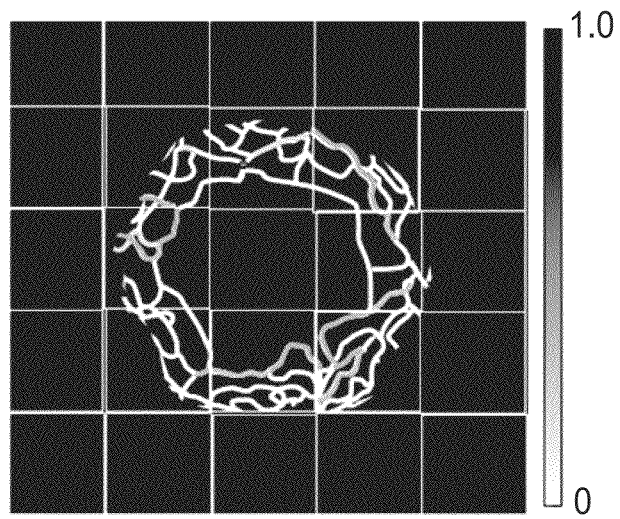
F I G. 10A
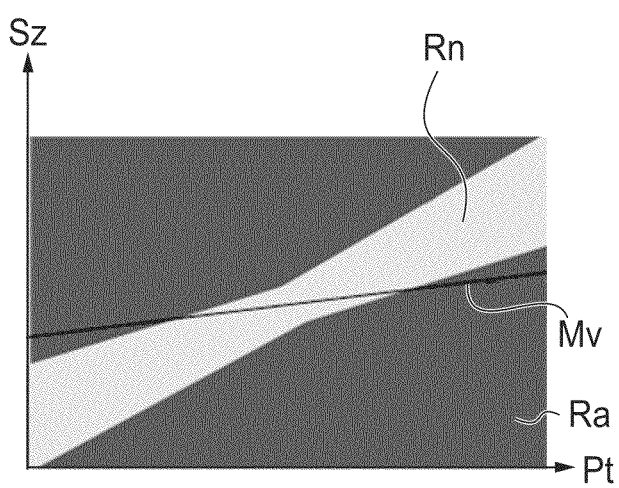
F I G. 10B

IMAGE PROCESSING APPARATUS AND IMAGE PROCESSING METHOD

BACKGROUND OF THE INVENTION

1. Field of the Invention

The present invention relates to an image processing apparatus and an image processing method used for ophthalmologic consultations.

2. Description of the Related Art

Ophthalmic examinations are widely performed for the purpose of early diagnosis of lifestyle-related diseases and diseases that rank highly among causes of loss of eyesight. A scanning laser ophthalmoscope (SLO), which is an image processing apparatus that uses the principle of a confocal laser microscope, is an apparatus that performs Raster scanning of an eye fundus using a laser that is a measuring beam and obtains a planar image at a high resolution and a high speed based on the intensity of the return light. The apparatus that captures this planar image will be referred to as an SLO apparatus, and the planar image will be referred to as an SLO image below.

In recent years, it has been possible to obtain a retinal SLO image with an improved horizontal resolution by increasing the diameter of the measuring beam in the SLO apparatus. However, there has been a problem in acquiring a retinal SLO image in that increasing the diameter of the measuring beam is accompanied by a decrease in the S/N ratio and in the resolution of the SLO image due to aberrations in the eye of the examination subject.

In order to resolve the above-mentioned problem, an adaptive optics SLO apparatus has been developed that has an adaptive optics system that measures aberrations in the eye of the examination subject in real-time using a wavefront sensor and corrects aberrations of a measuring beam or its return light that occur in the examination subject eye using a wavefront compensation device, thereby enabling the acquisition of an SLO image with a high horizontal resolution.

This SLO image having a high horizontal resolution can be acquired as a moving image, and in order to observe blood flow dynamics for example in a non-invasive manner, retinal blood vessels are extracted from the frames of the moving image, and the movement speed and the like of blood cells in capillaries are subsequently measured. Also, in order to evaluate the relationship between the photoreceptor cells and the visual function using the SLO image, photoreceptor cells P (as shown in FIG. 6B) are detected, and subsequently the density distribution and the alignment of the photoreceptor cells P are measured. FIG. 6B shows an example of an SLO image with a high horizontal resolution. The photoreceptor cells P, a low luminance region Q that corresponds to the position of a capillary, and a high-luminance region W that corresponds to the position of a leukocyte can be observed.

FIG. 6A shows an example of the various layers in the retina, from the inner limiting layer B1 to a pigmented layer B6. In the case of observing the photoreceptor cells P, measuring the distribution of photoreceptor cells P, or the like using the above-described SLO image, the focus position is set near the outer layer of the retina (B5 in FIG. 6A) and an SLO image such as FIG. 6B is captured. On the other hand, there are retinal blood vessels and bifurcated capillaries in the inner layers of the retina (B2 to B4 in FIG. 6A). 45% of the blood that is present in blood vessels is composed of blood cell components, and of those blood cell components, about 96% are erythrocytes and about 3% are leukocytes. An erythrocyte has a diameter of about 8 μm, and a neutrophil, which is the most common type of leukocyte, is about 12 to 15 μm in size.

As shown in FIG. 6C, if a leukocyte W is moving in a capillary in flow direction FD, small erythrocytes R flowing in the rear cannot pass the large leukocyte in the front, and therefore erythrocytes accumulate and an aggregation (hereinafter referred to as an "erythrocyte aggregate" DTi) forms behind the leukocyte. The size of the erythrocyte aggregate is at its smallest immediately subsequent to a vascular bifurcation (FIG. 6C), and it increases gradually as it nears the next vascular bifurcation (FIGS. 6D and 6E). Note that this aggregation occurs physiologically, and if the leukocyte is no longer in front of the erythrocyte aggregate, the erythrocytes will separate and move individually once again. If the focus position is set to the photoreceptor cells and an SLO image having a high horizontal resolution is acquired, the erythrocyte aggregate will be rendered as a dark tail behind the high-luminance leukocyte region W, as shown in FIG. 6F.

On the other hand, with a diabetic patient for example, erythrocytes will aggregate abnormally and form erythrocyte aggregates regardless of whether or not a leukocyte is present, as shown in FIG. 6G. Erythrocyte aggregates will be present at various positions in the capillary, including the position behind a leukocyte. Since the erythrocytes are constantly aggregated, the length of the erythrocyte aggregate behind the leukocyte will hardly change when moving between capillary bifurcations. Accordingly, by calculating the change in the size of the erythrocyte aggregate behind the leukocyte based on an SLO moving image with a high horizontal resolution, blood fluidity (the extent to which blood flows smoothly) can be measured in a non-invasive manner.

However, there has been a problem in that if the blood fluidity is to be measured, the capillary that is to be the target of analysis is selected manually, and therefore the procedure is cumbersome. Also, there has been a problem in that measurement values related to blood fluidity cannot be compared site-to-site. Therefore, a technique of (i) automatically selecting an analysis target blood vessel in order to measure the blood fluidity of an eye area, and (ii) displaying the distribution of the blood fluidity of the eye area is needed.

A conventional technique of generating a spatiotemporal image for a capillary branch region in an adaptive optics SLO moving image and measuring the degree of change in the length of the erythrocyte aggregate in the spatiotemporal image is disclosed in "Uji, Akihito, 'Observation of dark tail in diabetic retinopathy using adaptive optics scanning laser ophthalmoscope', Proceedings of the 66th Annual Congress of Japan Clinical Ophthalmology, p. 27 (2012)" as a technique for measuring blood fluidity in a non-invasive manner.

However, in the above-mentioned technique, the position of the capillary branch that is to be the position for measuring the length of the blood cell aggregate is specified manually, and there is a problem in that it is cumbersome to specify the capillary branch that is to be the measurement target from among the numerous capillary networks that are present in the parafovea.

SUMMARY OF THE INVENTION

The present embodiment has been created in view of the aforementioned problem and discloses an image processing apparatus and an image processing method for measuring blood fluidity in a simple and non-invasive manner by measuring the size of a blood cell aggregate.

According to one aspect of the present invention, there is provided an image processing apparatus comprising: an image obtaining unit configured to obtain an image of an eye area; an information obtaining unit configured to obtain information regarding a plurality of vascular branches that include a plurality of vascular bifurcations in the obtained image; a determining unit configured to determine a measurement target from the plurality of vascular branches based on the obtained information; and a measuring unit configured to measure the size of a blood cell aggregate in the determined measurement target.

Also, according to another aspect of the present invention, there is provided an image processing method comprising: a step of obtaining an image of an eye area; a step of obtaining information regarding a plurality of vascular branches that include a plurality of vascular bifurcations in the obtained image; a step of determining a measurement target from the plurality of vascular branches based on the obtained information; and a step of measuring the size of a blood cell aggregate in the determined measurement target.

Further features of the present invention will become apparent from the following description of exemplary embodiments with reference to the attached drawings.

BRIEF DESCRIPTION OF THE DRAWINGS

The accompanying drawings, which are incorporated in and constitute a part of the specification, illustrate embodiments of the invention and, together with the description, serve to explain the principles of the invention.

FIGS. 6A to 6G are diagrams for describing images acquired in the embodiment and blood cell dynamics.

FIGS. 10A and 10B are diagrams for describing display contents regarding measured values.

DESCRIPTION OF THE EMBODIMENTS

A preferred embodiment of the image processing apparatus and method according to the present invention will be described below in accordance with the accompanying drawings. Note that the present invention is not limited to the embodiment disclosed below.

The image processing apparatus according to the present embodiment has a configuration in which a vascular branch that is appropriate for measuring the size of a blood cell aggregate is automatically determined, whereafter change in the size of the blood cell aggregate that occurs when the blood cell aggregate moves in the vascular branch (between bifurcations) is measured, and the distribution of the measured values is displayed.

Specifically, the image processing apparatus extracts blood vessels from an SLO image Di and generates a composite image by compositing blood vessel images. A parafoveal region is specified based on the shape of an avascular region detected in the composite image, and a vascular branch candidate is extracted by determining a vascular bifurcation position in the parafoveal region. A case will be described below in which the vascular branch that is to be the measurement target is specified based on the shape of the vascular branch candidate and luminance change in the vascular branch, and on the shape of the path of the blood cell aggregate in the spatiotemporal image generated using the specified vascular branch; change in the size of the blood cell aggregate is measured; and the measured values are displayed as a map.

Overall Configuration

Figure 2:
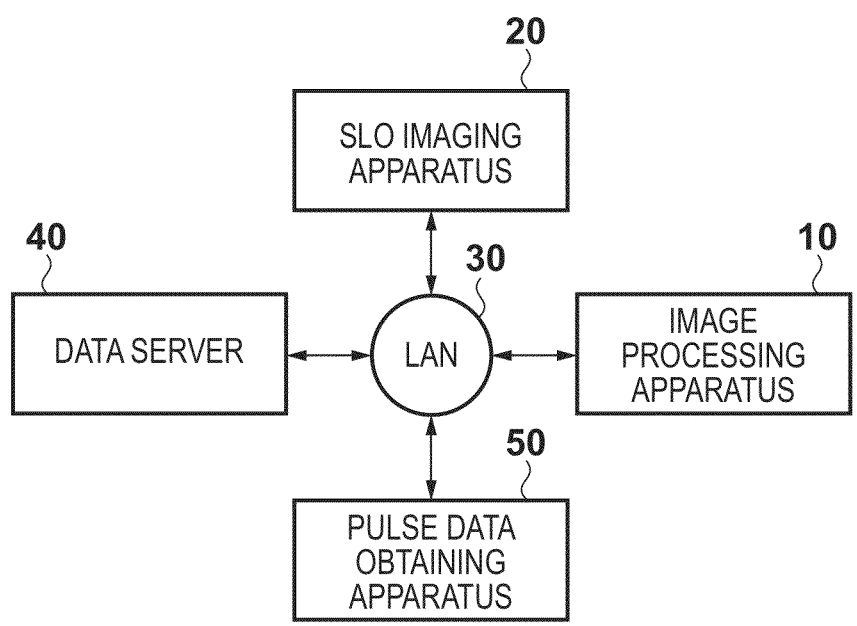
FIG. 2 is a block diagram showing an example of a functional configuration of a system that includes the image processing apparatus according to the embodiment.

FIG. 2 is a block diagram showing a configuration of a system that includes an image processing apparatus 10 according to the present embodiment. The image processing apparatus 10 is connected to an SLO imaging apparatus 20, a data server 40, and a pulse data obtaining apparatus 50 via a local area network (LAN) 30 configured by an optical fiber, a USB, an IEEE 1394, or the like. Note that a configuration is possible in which these devices are connected via an external network such as the Internet, and an alternative configuration is possible in which the image processing apparatus 10 is directly connected to the SLO imaging apparatus 20 and the like.

The SLO imaging apparatus 20 is an apparatus that captures the SLO image Di and transmits information regarding the SLO image Di and a fixation target position Fi that is used at the time of imaging to the image processing apparatus 10 and the data server 40.

Note that if the SLO image Di is obtained at a different magnification, it will be denoted as Dsi. That is to say, s is a variable indicating magnification, and i is a variable indicating image position number, and they are expressed as s=1, 2, . . . , smax, and i=1, 2, . . . , imax. As s increases, the imaging magnification increases (angle of view decreases).

The pulse data obtaining apparatus 50 is an apparatus that obtains biological signal data that changes autonomically, and is composed of a pulse wave meter or an electrocardiograph, for example. The pulse data obtaining apparatus 50 obtains pulse data while obtaining the above-mentioned SLO image Di according to an operation by an operator (not shown). Here, the pulse data is expressed as a sequence of points having the obtainment time t on one axis and the pulse wave signal value measured by the pulse wave meter on the other axis. The obtained pulse data is transmitted to the image processing apparatus 10 and the data server 40.

The data server 40 holds the SLO image Di of the examination subject eye, imaging condition data that is used at the time of imaging such as the fixation target position Fi and the pulse data, image characteristics of the eye area, parameter values for registering the positions of the SLO images Di, measured values for blood cell aggregate size, normal value range data for the measured values, and the like. Image characteristics for a capillary Q, a blood cell W, and retinal blood vessels are treated as image characteristics of the eye area in the present embodiment. The SLO image Di and the fixation target position Fi that is used at the time of imaging are output from the SLO imaging apparatus 20. The pulse data is output from the pulse data obtaining apparatus 50. Also, image characteristics of the eye area, registration parameter values for the SLO images Di, and measured values for the blood cell aggregate size are output from the image processing apparatus 10. Also, in response to a request from the image processing apparatus 10, the data server 40 transmits the SLO image Di, the fixation target position Fi, the pulse data, the eye area image characteristics, the registration parameter values, the measured values, and the normal value range data for the measured values to the image processing apparatus 10.

Figure 1:
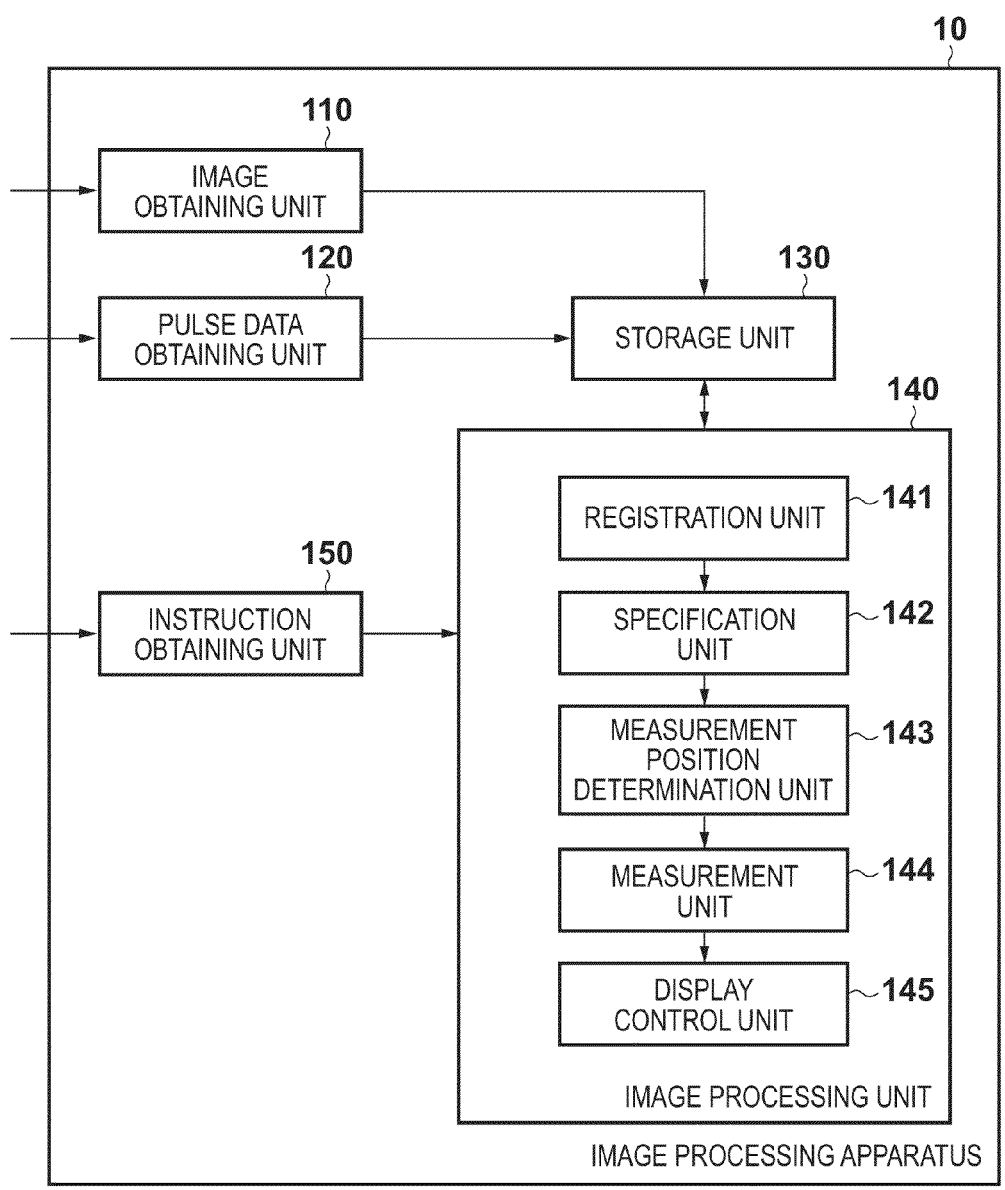
FIG. 1 is a block diagram showing an example of a functional configuration of an image processing apparatus according to an embodiment.

A functional configuration of the image processing apparatus 10 according to the present embodiment will be described next with reference to FIG. 1. FIG. 1 is a block diagram showing the functional configuration of the image processing apparatus 10, and the image processing apparatus 10 has an image obtaining unit 110, a pulse data obtaining unit 120, a storage unit 130, an image processing unit 140, and an instruction obtaining unit 150. Also, the image processing unit 140 includes a registration unit 141, a specification unit 142, a measurement position determination unit 143, a measurement unit 144, and a display control unit 145. The functions of the units will be described in detail later with reference to the flowchart in FIG. 5 and the like.

Figure 3:
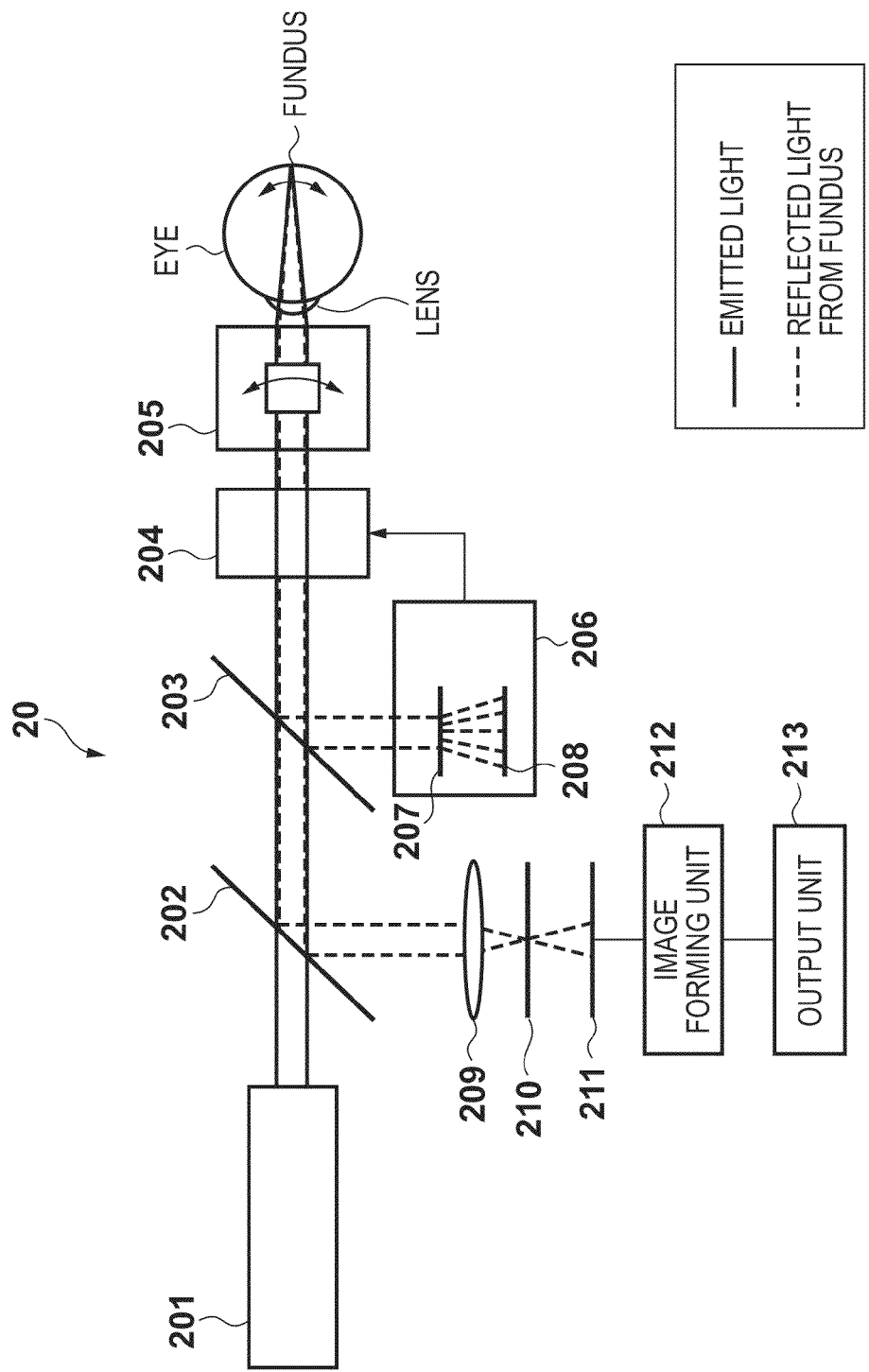
FIG. 3 is a diagram for describing an overall configuration of an SLO imaging apparatus according to the embodiment.

The configuration of an adaptive optics SLO (Adaptive Optics Scanning Laser Ophthalmoscope (AO-SLO)) will be described next with reference to FIG. 3. The AO-SLO 20 has an SLD (Super Luminescent Diode) 201, a Shack-Hartmann wavefront sensor 206, an adaptive optics system 204, beam splitters (202, 203), an X-Y scanning mirror 205, a focus lens 209, an aperture 210, a light sensor 211, an image forming unit 212, and an output unit 213.

Light that is emitted from the SLD 201, which is a light source, is reflected by the eye fundus, a portion of that light is input to the Shack-Hartmann wavefront sensor 206 via the second beam splitter 203, and the rest is input to the light sensor 211 via the first beam splitter 202. The Shack-Hartmann wavefront sensor 206 is a device for measuring eye aberrations and has a lens array 207 and a CCD 208. When incident light passes through the lens array 207, a cluster of light spots appears on the CCD 208, and a wavefront aberration is measured based on the shift in the positions of the projected light spots. The adaptive optics system 204 drives an aberration correction device (a deformable mirror or a space/light phase modulator) based on the wavefront aberration measured by the Shack-Hartmann wavefront sensor 206 and corrects the aberration. The light that has undergone aberration correction is received by the light sensor 211 via the focus lens 209 and the aperture 210. The scanning position on the eye fundus can be controlled by moving the X-Y scanning mirror 205, and data corresponding to time (number of frames/frame rate) and the imaging target region that was designated in advance by the operator is obtained. The data is transferred to the image forming unit 212, image deformities caused by variation in the scanning speed are corrected, luminance values are corrected, and image data (moving image or still image) is formed. The output unit 213 outputs the image data formed by the image formation unit 212. In order to set the focus to a specified depth position in the eye fundus, at least one of the following types of adjustment can be used: adjustment using an aberration correction device in the adaptive optics system 204, and adjustment performed by installing a focus adjustment lens (not shown) in the optical system and moving that lens.

Figure 4:
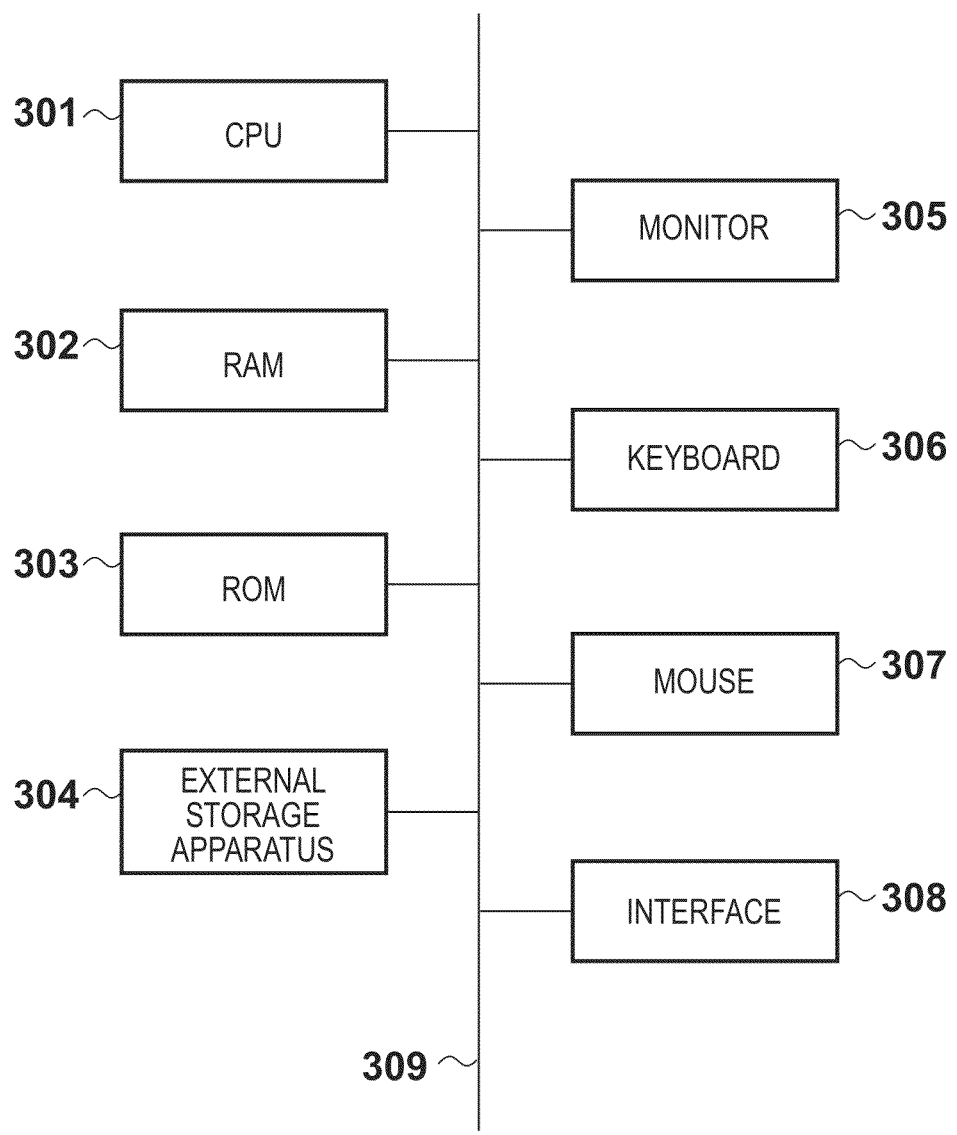
FIG. 4 is a block diagram showing an example of a hardware configuration of an image processing apparatus according to the embodiment.

A hardware configuration of the image processing apparatus 10 will be described next with reference to FIG. 4. In FIG. 4, reference numeral 301 is a central processing unit (CPU), reference numeral 302 is a memory (RAM), reference numeral 303 is a control memory (ROM), reference numeral 304 is an external storage apparatus, reference numeral 305 is a monitor, reference numeral 306 is a keyboard, reference numeral 307 is a mouse, and reference numeral 308 is an interface. The external storage apparatus 304 stores a control program for realizing an image processing function according to the present embodiment and data that is used when the control program is executed. The control program and the data are stored in the appropriate RAM 302 via a bus 309, are executed by the CPU 301, and function as the elements of the functional configuration shown in FIG. 1 under the control of the CPU 301.

Figure 5:
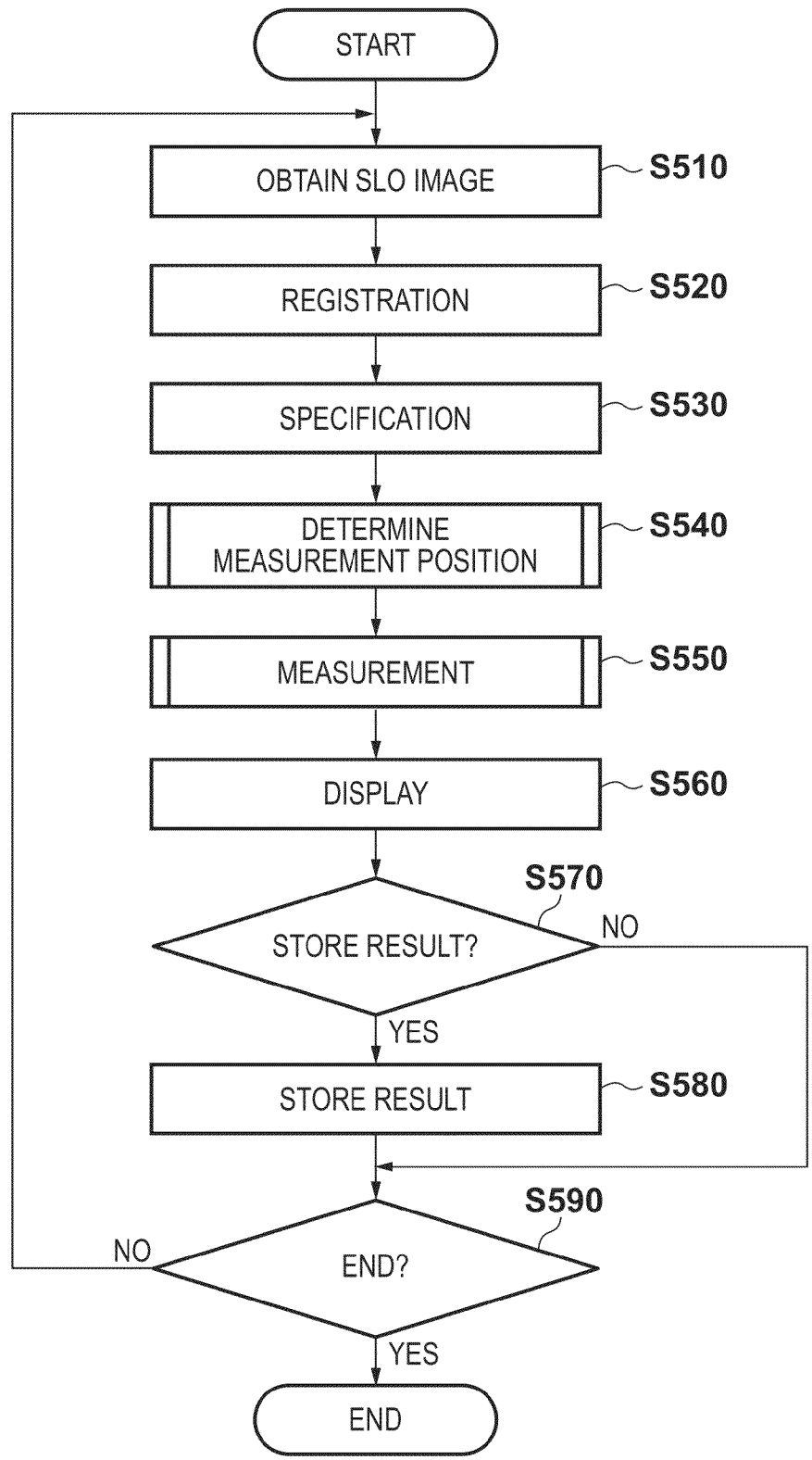
FIG. 5 is a flowchart of processing executed by the image processing apparatus according to the embodiment.

Functions of the blocks that configure the image processing apparatus 10 shown in FIG. 1 will be described below in association with a specific execution procedure of the image processing apparatus 10 shown in the flowchart in FIG. 5.

Step S510

The image obtaining unit 110, which is an example of an image obtaining means for obtaining an image of an eye area, makes a request to the SLO imaging apparatus 20 to obtain an SLO image Dsi and a fixation target position Fsi. In the present embodiment, a low-magnification SLO image D1 is obtained by setting a fixation target position F1 to the fovea in the macular region, and a high-magnification SLO image D2$i$ is obtained by setting a fixation target position F2$i$ to the foveal and parafoveal regions. Note that the method for setting the imaging position is not limited to this, and a setting of any position may be used.

Also, the pulse data obtaining unit 120 makes a request to the pulse data obtaining apparatus 50 to obtain pulse data related to biological signals. In the present embodiment, a pulse wave meter is used as the pulse data obtaining apparatus, and pulse wave data is obtained from an earlobe of the examination subject. The pulse data obtaining apparatus 50 obtains the corresponding pulse data and transmits it according to the acquisition request, and thereby the pulse data obtaining unit 120 receives the pulse wave data from the pulse data obtaining apparatus 50 via the LAN 30. The pulse data obtaining unit 120 stores the received pulse data in the storage unit 130.

Here, consideration will be given to the case where the image obtaining unit 110 starts to obtain the SLO image Di according to the phase of the pulse data obtained by the pulse data obtaining apparatus 50, and the case where the acquisition of the pulse data and the acquisition of the SLO image Di are started at the same time immediately subsequent to receiving a request to obtain the SLO image Di. In the present embodiment, immediately subsequent to receiving a request to obtain the SLO image Di, the acquisition of the pulse data and the SLO image Di is started.

In response to the obtainment request, the SLO imaging apparatus 20 obtains and transmits the SLO images D1 and D2$i$ and the fixation target positions F1 and F2$i$, and thereby the image obtaining unit 110 receives the SLO images D1 and D2$i$ and the fixation target positions F1 and F2$i$ from the SLO imaging apparatus 20 via the LAN 30. The image obtaining unit 110 stores the received SLO images D1 and D2$i$ and the fixation target positions F1 and F2$i$ in the storage unit 130. Note that in the present embodiment, the SLO images D1 and D2$i$ are moving images whose frames have been registered.

Step S520

The registration unit 141 registers the SLO image D1 and the SLO images D2$i$ and obtains the relative positions of the SLO images D2$i$ in the SLO image D1.

If there is an overlapping region in the SLO images D2$i$, the degree of image similarity is first calculated for the overlapping region, and the positions of the SLO images D2$i$ are registered at the position at which the degree of image similarity is the largest.

Also, if three or more SLO images with different magnifications are obtained in step S510, registration is performed in sequence starting from the SLO image having the lowest magnification. For example, if the SLO image D1, the SLO images D2$i$, and SLO images D3$i$ are obtained, registration between the SLO image D1 and the SLO images D2$i$ is performed, and subsequently, registration between the SLO images D2$i$ and the SLO images D3$i$ is performed.

Note that the registration unit 141 obtains the fixation target position F2$i$ that is used at the time of capturing the SLO image D2$i$ from the memory unit 130 and uses it as the initial point in the search for registration parameters in the registration between the SLO image D1 and the SLO image D2$i$. Also, any method can be used as the method for image similarity degree and coordinate conversion, and in the present embodiment, registration is performed using a correlation coefficient for the degree of image similarity and Affine conversion is used as the coordinate conversion method.

A composite image of the SLO images D2$i$ is generated using information (registration parameters) regarding the relative positions of the SLO images D2$i$ in the SLO image D1 that was obtained in the present step.

Step S530

In the specification unit 142, a vascular region in the retina is specified from the SLO images D2$i$. In the present embodiment, as an example of vascular region specification processing for specifying a vascular region based on the change over time in the luminance values of a moving image of an eye area, processing is used in which a vascular region is specified as the movement range of blood cell components from the SLO images D2$i$ using the procedure below.

(a) Perform subtraction processing between sequential frames of an intermediate-scale image D2$i$ whose frames have been registered (generate differential moving image).

(b) Calculate luminance value statistic (variance) for the frame direction at the x-y positions of the differential moving image generated in (a).

(c) Specify the region in which the luminance variance is at or above a threshold value Tv at the x-y positions of the differential moving image as the region in which blood cells are moving, or in other words, as the vascular region.

Note that the blood vessel detection processing for specifying the vascular region is not limited to this method, and any method may be used. For example, in (a) above, division processing for the luminance values between sequential frames may be used (generating a division moving image) instead of using subtraction. Alternatively, a blood vessel may be detected with the application of a filter that enhances linear structures in a specific frame of the SLO image D1 or the SLO image D2$i$.

Note that the image obtained by specifying the vascular region out of the SLO images D2$i$ is denoted below as the blood vessel image V2$i$. Also, a composite image of the blood vessel image V2$i$ is generated using the registration parameter values obtained in step S520.

Step S540

The measurement position determination unit 143 automatically determines a vascular branch that is to be the target when measuring the change in the size of a blood cell aggregate. The processing of the present step will be described in detail later with reference to the flowchart in FIG. 8. Note that the measurement position determination unit 143 is an example of an information obtaining means for obtaining information related to multiple vascular branches that include multiple vascular bifurcations in the obtained image (SLO image), and a determining means for determining a measurement target out of the multiple vascular branches based on the obtained information.

Step S550

The measurement unit 144, which is an example of a measuring means for measuring the size of a blood cell aggregate in a measurement target, measures a value for the change in the size of the blood cell aggregate in the vascular branch determined in step S540. The processing of the present step will be described in detail later with reference to the flowchart in FIG. 9.

Step S560

The display control unit 145, which is an example of a display control means, displays the measured value for the change in the size of the blood cell aggregate that was obtained in step S550, and a diagram generated based on that measured value on the monitor 305.

In the present embodiment, the display control unit 145 colorizes the measured values for the change in the size of the blood cell aggregate in the vascular branches that are the measurement targets determined in step S540 as shown in FIG. 10A, and displays them as a map (note that the illustration is monochrome (greyscale)). Accordingly, the distribution of measured values for the change in the size of the blood cell aggregate can be listed and understood. Note that the method of displaying the distribution of measured values is not limited to a color display, and for example, it is possible to display them as density values, and they may be included as measured values as well.

Note that the measured value is not limited to a value for the change in the blood cell aggregate size in vascular branches that are measurement targets. For example, it is possible to perform display in a display mode of mapping and displaying a difference (e.g. a deviation) from a normal value (statistical value) that was calculated based on a value within a range of normal values for the elongation rate of the size of the blood cell aggregate.

Also, as the display mode for displaying the change in the size of the blood cell aggregate with respect to the vascular branch designated by a user, a graph (FIG. 10B) is displayed in which the position in the vascular branch (Pt) is indicated by the horizontal axis, the blood cell aggregate size (Sz) is indicated by the vertical axis, and the blood cell aggregate size (Mv) is plotted along with a range of normal values (Rn) and a range of abnormal values (Ra). According to this, it is possible to check whether or not there is a problem by comparing the degree of change in the blood cell aggregate size with the range of normal values.

Figure 7A:
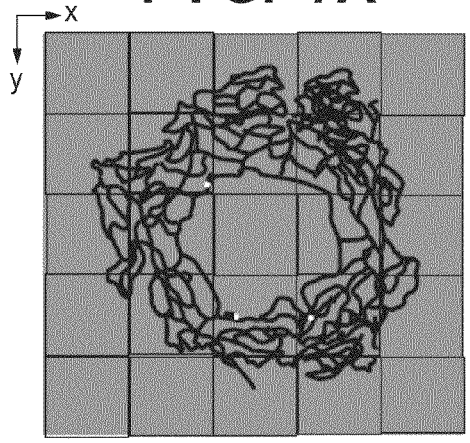
FIGS. 7A to 7F are diagrams for describing image processing contents of the embodiment.

Furthermore, the display control unit 145 generates a superimposed image in which the SLO images D2$i$ are superimposed on an SLO image D11 as shown in FIG. 7A based on the registration parameter values obtained in step S520 and displays the superimposed image. Here, the playback timings of the SLO images D11 and D2$i$ are synchronized based on the pulse data (cycle data based on a biological signal such as a pulse wave) and displayed. Specifically, the display control unit 145 obtains pulse data corresponding to the SLO images D11 and D2$i$ from the storage unit 130, detects the respective peak values in the pulse data, and thereby calculates a beat cycle. Next, in order to deal with the case where the beat cycle is different between SLO images, adjustment processing for the display frame interval between the images (frame interpolation processing) is performed. Furthermore, composite video display is performed by playing back frames for an integer number of beat cycles while adjusting the playback start times of the moving images such that the playback timings of frames corresponding to peak values of the pulse data corresponding to the moving images are synchronized.

Note that in an image whose frames have been registered, there are cases where visibility is reduced due to regions having a pixel value of 0 appearing at the edge regions of the image, and therefore only pixels having pixel values greater than 0 are displayed in all frames at the time of composite display. If the pulse data has not been obtained, this step is not performed, and the moving image may undergo composite display without the playback start times being adjusted. The distribution of the amount of change in the blood cell aggregate size can be understood quantitatively according to the map of the amount of change in the size of the blood cell aggregate while the dynamics of the blood cell aggregate are understood intuitively according to the composite moving image.

Note that the display control that can be used in the present embodiment is not limited to the above description, and it is possible to perform any type of display that is based on the measured values of the blood cell aggregate size.

Step S570

The instruction obtaining unit 150 obtains an instruction from the exterior about whether or not to store the SLO images D1 and D2$i$, the fixation target positions F1 and F2$i$, pulse wave analysis data, the registration parameter values, the blood vessel image V2$i$, the measurement target position, and measured values relating to the blood cell aggregate size in the data server 40. This instruction is input by the operator via the keyboard 306 or the mouse 307 for example. If storage is instructed, the procedure moves to the processing of step S580, and if storage is not instructed, the procedure moves to step S590.

Step S580

The image processing unit 140 transmits the examination date/time, information for identifying the examination subject eye, SLO images D1 and D2$i$, the fixation target positions F1 and F2$i$, pulse wave analysis data, the registration parameter values, the blood vessel image V2$i$, the measurement target position, and measured values relating to the blood cell aggregate size to the data server 40 in association with each other.

Step S590

The instruction obtaining unit 150 obtains an instruction from the outside regarding whether or not to end the processing related to the SLO image D2$i$ according to the image processing apparatus 10. This instruction is input by the operator via the keyboard 306 or the mouse 307. If an instruction to end processing is obtained, the processing ends. On the other hand, if an instruction to continue processing is obtained, the procedure returns to the processing of step S510 and processing for the next examination subject eye (or reprocessing for the same examination subject eye) is performed.

Figure 8:
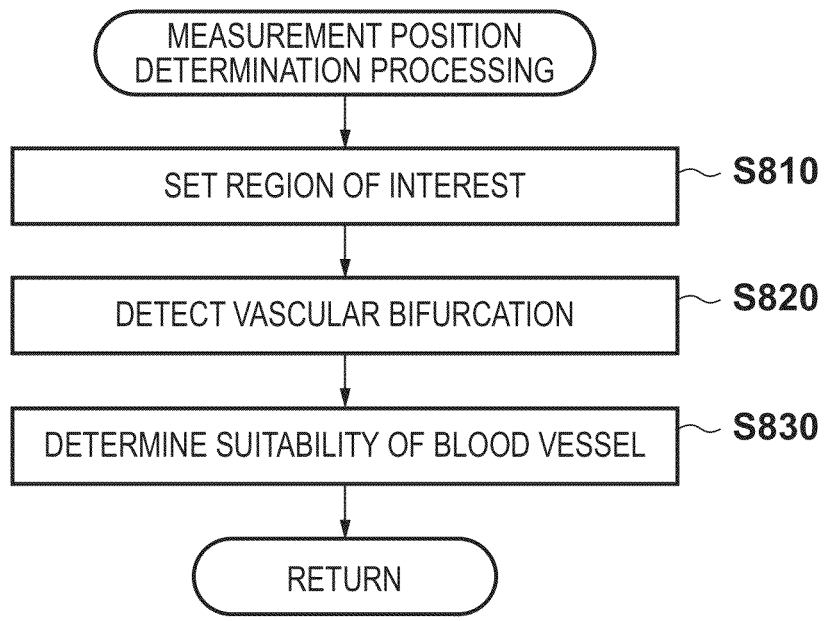
FIG. 8 is a flowchart showing details of measurement position determination processing according to the embodiment.

The details of the measurement position determination processing executed by the measurement position determination unit 143 in step S540 will be described next with reference to the flowchart shown in FIG. 8.

Step S810

In the present embodiment, the measurement position determination unit 143 executes region-of-interest specification processing for specifying a region of interest in which a measurement target vascular branch is to be specified. An example of region-of-interest specification processing will be described below. The measurement position determination unit 143 determines a region of interest (ROI) based on the vascular region obtained in step S530. In the present embodiment, the ROI related to the parafovea is set as described below. Specifically, the border of an avascular region is detected from the vascular region obtained in step S530.

Figure 7B:
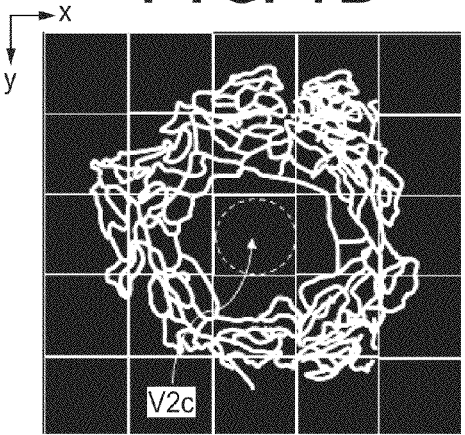

In the vicinity of the retinal fovea, a region in which there are no retinal blood vessels (an avascular region) is present (black, enclosed region in the central portion of FIG. 7B). It should be noted that the avascular region near the foveal may be referred to as (Foveal Avascular Zone) FAZ. There is significant individual variation in the shape of the border of the avascular region, and primary lesions in the retinal blood vessels tend to appear in the periphery of the border of the avascular region. In particular, capillaries belonging to the avascular region border are where vascular lesions appear the earliest, and the avascular region border is important as a target for observation and analysis. Note that it is known that the blood vessels at the avascular region border are thin compared to surrounding areas.

Figure 7C:
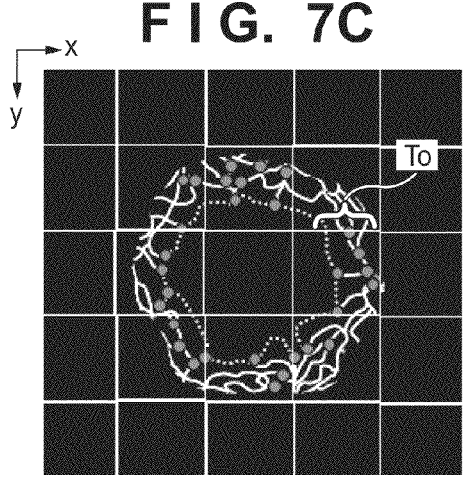

In the present embodiment, in a blood vessel image V2$c$ that is positioned in the center of FIG. 7B, a model of varying shape (dotted-line portion in same drawing) that corresponds to the inscribed circle in the blood vessel image V2$c$ is arranged on the composite image for the blood vessel image V2$i$. After deformation is complete, the deformable model is positioned on the avascular region border (dotted line portion in FIG. 7C). A position on the outer side at a distance of a threshold value To from the avascular region border is determined using a distance image (image that has a distance value from the border in its pixel value) that is obtained by furthermore performing Euclidean distance conversion on the avascular region border. Although any value can be set as the threshold value To, it is generally set to around 150 (μm) for a healthy person, and therefore that value will be used in the present embodiment as well. As shown in FIG. 7C, an annular (doughnut-shaped) region of interest is determined using the two specified borders, namely an inner border and an outer border.

Note that in the present embodiment, the circular region at a distance of the threshold value To from the avascular region border was set as the region of interest, but the present invention is not limited to this.

For example, it is possible to set only a capillary (dotted line portion in FIG. 7C) that belongs to the avascular region border as the region of interest. The capillary belonging to the avascular region border is where vascular lesions appear the earliest, and is a region of interest at which measurement of the change in the blood cell aggregate size can be performed most readily.

Alternatively, although the width of the annular region that is to be the region of interest was fixed at a threshold value To, the present invention is not limited to this. For example, with a disease such as diabetic retinopathy, where lesions appear in retinal capillaries in the parafovea, capillaries are obstructed as the disease progresses and the avascular region increases in size. Also, if the avascular region increases in size, vascular lesions may possibly occur in a range wider than the periphery of the avascular region. Therefore, a value obtained by multiplying a value that is proportional to the area of the avascular region to the threshold value To may be set as the distance from the avascular region border, and thereby the annular region of interest may be determined.

Step S820

The measurement position determination unit 143 executes vascular bifurcation specification processing for specifying multiple vascular bifurcations from multiple blood vessels. In the present embodiment, processing for detecting a bifurcation position (vascular bifurcation) from a vascular region in the region of interest set in step S810 will be performed as an example of the vascular bifurcation specification processing.

In the present embodiment, the position of a vascular bifurcation needs to be specified since the change in the size of the blood cell aggregate at a bifurcation such as that shown in FIGS. 6C to 6E is to be measured. However, due to the fact that there are cases where a blood vessel appears to include a bifurcation when in actuality it is merely an intersection of two blood vessels, the bifurcation areas need to be correctly specified after being distinguished from intersections.

Specifically, thinning processing is performed first on a vascular region in the region of interest and bifurcations are determined based on the continuity of white pixels (pixels whose pixel value is not 0) in the obtained binary image. In the present embodiment, if there are three white pixels among the pixels adjacent to the white pixel that is the determination target, it is determined as a bifurcation, and if there are four white pixels, it is determined as an intersection, and thereby the bifurcation positions as indicated by the round marks in FIG. 7C are determined.

Step S830

Among the blood vessels in the region of interest, the measurement position determination unit 143 determines regions having the bifurcation positions determined in step S820 at both ends as vascular branch candidates in the vascular images V2i. Next, among the vascular branch candidates, a vascular branch candidate that satisfies the following conditions is determined as the measurement target vascular branch.

i) the length of the vascular branch candidate is greater than or equal to the threshold value Tl ii) the diameter (width) of the vascular branch candidate is within a predetermined range (greater than or equal to a threshold value Tmin, less than a threshold value Tmax).

According to the description above, a region including neighboring vascular bifurcations with a blood vessel therebetween is taken as one vascular branch, vascular branch specification processing for specifying multiple vascular branches (vascular branch candidates) is executed, and a measurement target is determined based on information (length, diameter) regarding the vascular branch candidate.

Here, i) corresponds to the fact that in order for the blood cell aggregate size to change, the blood vessel length needs to be a certain distance. For example, in the case of observing change in the blood cell aggregate size, with consideration given to the ultimate length of the blood cell aggregate, it is preferable that the blood vessel length is at least 100 μm. Also, ii) is based on the fact that there is a limitation on how small the diameter of the capillary that allows the leukocyte to pass through is, and is furthermore based on a constraint that if the capillary diameter is excessively larger than the size of the leukocyte, erythrocytes will block incident light and the position of the leukocyte cannot be specified. For example, it is preferable that the vascular diameter of the vascular branch is about 10 μm to about 20 μm due to the fact that the erythrocyte diameter is about 8 μm and that neutrophils, which are the most common type of leukocyte, are 12 to 15 μm in size. Note that the vascular branch that is to be the measurement target may be selected using one of conditions i) and ii). The measurement target is determined based on information values (vascular branch length or vascular diameter) regarding the vascular branch from among the vascular branches that are thus specified based on the vascular bifurcation.

Note that the method for determining the measurement target vascular branch is not limited to this. In addition to the above-described conditions for the vascular branches, it is possible to use information regarding chronological luminance values in the specified vascular region (difference between or distribution of chronological luminance values in the specified vascular region). For example, an additional condition (for determining a measurement target vascular branch) may be used in which a vascular branch is used that, in the same location throughout all frames calculated in step S530, has a) a variance in luminance values that is greater than or equal to the threshold value Tv, or b) a difference between the largest and smallest luminance values that is greater than or equal to the threshold value Ts.

This is a condition that is set in order to narrow down the numerous vascular branch candidates to capillary branches that leukocytes and blood cell aggregates pass through. This condition corresponds to the fact that the value of a) or b) above increases in capillaries that the leukocyte and the blood cell aggregate pass through since the luminance is highest at the time of passing of the leukocyte, and the luminance is lowest at the time of passing of the blood cell aggregate.

Figure 9:
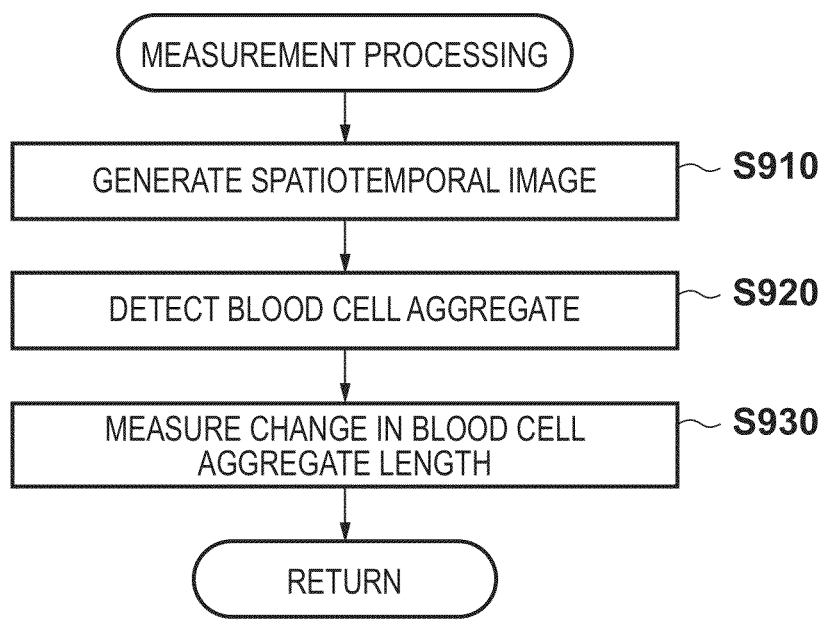
FIG. 9 is a flowchart showing details of measurement processing according to the embodiment.

The details of the measurement processing executed in step S550 will be described next with reference to the flowchart shown in FIG. 9.

Step S910

Figure 7D:
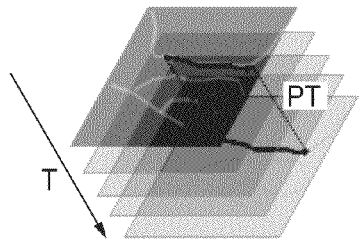
Figure 7E:
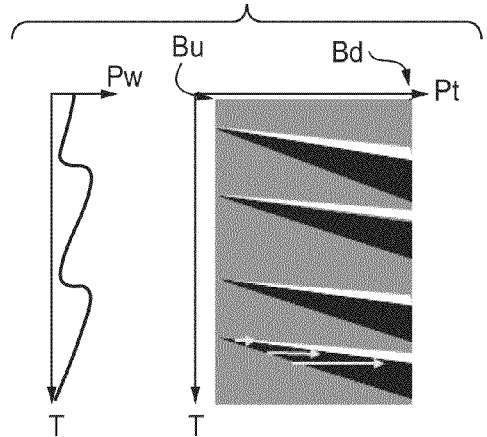
Figure 7F:
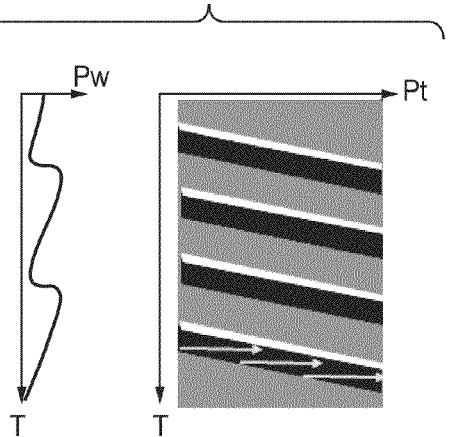

The measurement unit 144 generates a spatiotemporal image such as that shown in FIG. 7E or FIG. 7F with the vascular branch (length PT) that was determined as the measurement target. The spatiotemporal image includes the position Pt in the vascular branch on its horizontal axis and the scanning time T on its vertical axis, and corresponds to the fact that a curved cross-sectional image of the SLO image (whose frames have been registered) taken along the designated vascular branch is generated (FIG. 7D). Note that the horizontal axis of the spatiotemporal image is set such that the side that is close to the origin is the upstream side (Bu), and the side that is far from the origin is the downstream side (Bd). The graphs in FIGS. 7E and 7F also show the pulse cycle Pw associated with the vascular branch position Pt and obtained by the pulse data obtaining apparatus 50.

The spatiotemporal image includes a high-luminance linear component that indicates the movement of the leukocyte, and a low-luminance linear component that indicates the movement of the erythrocyte aggregate that is present immediately rearward of the leukocyte.

Step S920

The measurement unit 144 specifies a leukocyte based on a luminance value that is greater than or equal to a threshold value in the measurement target and subsequently performs blood cell aggregate specification processing for specifying an adjacent blood cell aggregate. An example of the blood cell aggregate specification processing of the present embodiment executed in step S920 will be described below. The measurement unit 144 detects a measurement target blood cell aggregate in the spatiotemporal image generated in step S910. In the present embodiment, the blood cell aggregate rearward of the leukocyte is the measurement target, and therefore the movement path of the high-luminance leukocyte is detected first from the spatiotemporal image, and the low-luminance region directly below the high-luminance path is detected as the blood cell aggregate.

Specifically, line enhancement is performed using any line enhancement filter, and the high-luminance leukocyte path is detected by binarizing using a threshold value Tt1. Furthermore, the low-luminance blood cell aggregate path is detected by binarizing the low-luminance region adjacent to the detected high-luminance region using a threshold value Tt2. The method for detecting the blood cell aggregate is not limited to the above-described method, and any image processing method may be used.

Next, in order to prevent the blood cell aggregate shape measurement result from being influenced by the heartbeat, only a blood cell aggregate path that corresponds to a specific phase section of the pulse data is selected out of the detected blood cell aggregate paths as the measurement target. Here, the measurement unit 144 obtains pulse data corresponding to the SLO image D2*i* in advance from the storage unit 130 and detects the peak values of the pulse data. In the present embodiment, as a blood cell aggregate path corresponding to a phase section that does not include rising portions in the pulse data, the fourth blood cell aggregate from the top in FIGS. 7E and 7F is selected as the measurement target.

Step S930

The measurement unit 144 measures the change in the size of the movement path of the blood cell aggregate that was detected and selected in step S920. In the present embodiment, the length (length in the horizontal direction in the spatiotemporal image) in the direction of the central axis of the blood vessel of the blood cell aggregate is measured as the blood cell aggregate size (length of arrows in FIGS. 7E and 7F), and the elongation rate of the blood cell aggregate is calculated according to the following equation.

(size of blood cell aggregate near downstream bifurcation−size of blood cell aggregate near upstream bifurcation)/(length of vascular branch)  (1)

Note that the size of the above-described erythrocyte aggregate may be measured using the following method. That is to say, the slope (angle) of the erythrocyte aggregate movement path is calculated using a Hough transformation, and the movement speed of the erythrocyte aggregate is calculated based on that angle. Next, the erythrocyte aggregate length is measured as:

(blood cell aggregate movement speed)×(time it takes for blood cell aggregate to pass a certain position in the vascular branch)  (2)

That is to say that in the case of observing the movement of the erythrocyte aggregate at a certain position in the vascular branch at a fixed point, it is presumed that the erythrocyte aggregate will pass the observation point at a fixed movement speed (which was calculated based on the slope of the movement path), and thereby the length of the erythrocyte aggregate is measured by calculating equation (2). This corresponds to the fact that the length in the vertical direction of the movement path for the erythrocyte aggregate is measured in the spatiotemporal image.

Also, the measured value for the change in the blood cell aggregate size is not limited to being calculated using the rate of elongation in the vertical direction or the horizontal direction of the blood cell aggregate in the spatiotemporal image between the vicinity of an upstream bifurcation and the vicinity of a downstream bifurcation. For example, it is possible to calculate a value obtained by determining the difference between lengths of the blood cell aggregate in the vicinity of upstream bifurcations for each point in the vascular branch and integrating them. By calculating this integrated value, a measurement that reflects more precise changes in the blood cell aggregate length can be performed. Alternatively, the size of the blood cell aggregate may be calculated based on a value measured directly in a frame of the SLO image D2*i* without the spatiotemporal image being generated.

Alternatively, a deviation from a normal value may be calculated based on a value that is within a normal range of values for the elongation rate of the blood cell aggregate size.

According to the above-described configuration, the image processing apparatus 10 automatically determines a vascular branch that is appropriate for measuring the blood cell aggregate size, subsequently measures the change in the size of the blood cell aggregate in the vascular branch (between bifurcations), and displays a distribution of the measured values. Accordingly, after a measurement target vascular branch is specified in a simple manner, blood fluidity can be measured non-invasively.

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The above-described processing method can be applied to a portion other than a retina. For example, the above-described processing method can be applied to anterior eye part.

This application claims the benefit of Japanese Patent Application No. 2013-040039, filed Feb. 28, 2013, which is hereby incorporated by reference herein in its entirety.

What is claimed is:

1. An image processing apparatus comprising:
   an image obtaining unit configured to obtain an image of an eye area;
   an information obtaining unit configured to obtain information regarding a plurality of vascular branches that include a plurality of vascular bifurcations in the obtained image;
   a determining unit configured to determine a measurement target from the plurality of vascular branches based on the obtained information; and
   a measuring unit configured to measure the size of a blood cell aggregate in the determined measurement target.

2. The apparatus according to claim 1, wherein the information obtaining unit obtains at least one value out of a length and a diameter of the plurality of vascular branches as the information regarding the plurality of vascular branches, and
   wherein the determining unit determines the measurement target from the plurality of vascular branches based on the obtained value.

3. The apparatus according to claim 2, further comprising:
   a vascular branch specifying unit configured to specify the plurality of vascular branches using a region that includes two neighboring vascular bifurcations out of the plurality of vascular bifurcations and a blood vessel between the two vascular bifurcations as one vascular branch, wherein the information obtaining unit obtains at least one out of the lengths and the vascular diameters of the specified plurality of vascular branches.

4. The apparatus according to claim 2, wherein the determining unit determines a vascular branch among the plurality of vascular branches whose vascular diameter is within a predetermined range as the measurement target.

5. The apparatus according to claim 2, wherein the image obtaining unit obtains a moving image of the eye area as the image, and wherein the measuring unit measures change in the size of the blood cell aggregate based on the obtained value.

6. The apparatus according to claim 5, further comprising:
a vascular region specifying unit configured to specify a vascular region from the obtained moving image based on change in luminance values in the obtained moving image; and
a vascular bifurcation specifying unit configured to specify the plurality of vascular bifurcations from the specified vascular region.

7. The apparatus according to claim 6, further comprising:
a region-of-interest specifying unit configured to specify a region of interest from the obtained moving image based on the specified vascular region and a parafoveal region in the eye area,
wherein the vascular bifurcation specifying unit specifies the plurality of vascular bifurcations from the specified region of interest,
wherein the information obtaining unit furthermore obtains information regarding a luminance value in the specified region of interest, and
wherein the determining unit determines the measurement target from the specified plurality of vascular branches based on the obtained value and the information regarding the luminance value.

8. The apparatus according to claim 7, wherein the obtained information regarding the luminance value is the difference between luminance values or the distribution of luminance values in the specified region of interest.

9. The apparatus according to claim 6, further comprising:
a vascular region specifying unit configured to specify an avascular region border from the obtained image based on the parafoveal region of the eye area,
wherein the vascular bifurcation specifying unit specifies the plurality of vascular bifurcations from the specified avascular region border.

10. The apparatus according to claim 1, further comprising:
a blood cell aggregate specifying unit configured to specify the blood cell aggregate based on a luminance value that is at or above a threshold value in the determined measurement target,
wherein the measuring unit measures the length of the specified blood cell aggregate as the size.

11. The apparatus according to claim 1, further comprising:
a display control unit configured to cause a display mode to be displayed on a display unit, the display mode indicating at least one of the measured size and a deviation from a statistical value for the size.

12. The apparatus according to claim 11, wherein the display control unit causes the display mode and a normal value range to be displayed on the display unit.

13. An image processing method comprising:
a step of obtaining an image of an eye area;
a step of obtaining information regarding a plurality of vascular branches that include a plurality of vascular bifurcations in the obtained image;
a step of determining a measurement target from the plurality of vascular branches based on the obtained information; and
a step of measuring the size of a blood cell aggregate in the determined measurement target.

14. The method according to claim 13, wherein in the step of obtaining information, at least one value out of the length and the vascular diameter of the plurality of vascular branches is obtained as the information regarding the plurality of vascular branches, and
wherein in the step of determining, the measurement target is determined from the plurality of vascular branches based on the obtained value.

15. The method according to claim 14, further comprising:
a step of specifying the plurality of vascular branches using a region that includes two neighboring vascular bifurcations out of the plurality of vascular bifurcations and a blood vessel between the two vascular bifurcations as one vascular branch,
wherein in the step of obtaining information, at least one value out of the lengths and the vascular diameters of the specified plurality of vascular branches is obtained.

16. The method according to claim 14, wherein in the step of obtaining the image, a moving image of the eye area is obtained as the image, and
wherein in the step of measuring, change in the size of the blood cell aggregate is measured based on the obtained value.

17. A non-transitory computer-readable storage medium storing a program for causing a computer to execute a method comprising:
obtaining an image of an eye area;
obtaining information regarding a plurality of vascular branches that include a plurality of vascular bifurcations in the obtained image;
determining a measurement target from the plurality of vascular branches based on the obtained information; and
measuring the size of a blood cell aggregate in the determined measurement target.

* * * * *